United States Patent
Chau

(10) Patent No.: US 7,465,296 B2
(45) Date of Patent: Dec. 16, 2008

(54) HOT MEDICAL COMPRESS APPARATUS

(76) Inventor: Hang Chun Chau, Flat A2, 15/F, Cambridge Court, 84 Waterloo Road, Kowloon (HK)

(*) Notice: Subject to any disclaimer, the term of this patent is extended or adjusted under 35 U.S.C. 154(b) by 290 days.

(21) Appl. No.: 10/558,368

(22) PCT Filed: May 31, 2004

(86) PCT No.: PCT/CN2004/000566

§ 371 (c)(1),
(2), (4) Date: Sep. 19, 2006

(87) PCT Pub. No.: WO2004/105675

PCT Pub. Date: Dec. 9, 2004

(65) Prior Publication Data

US 2008/0045910 A1    Feb. 21, 2008

(30) Foreign Application Priority Data

May 30, 2003    (CN) ............................... 03 1 26716

(51) Int. Cl.
*A61F 7/00* (2006.01)
(52) U.S. Cl. .................. 604/291; 604/290; 604/292; 604/293; 601/19; 601/20; 601/27; 601/28; 601/52; 601/53; 601/94; 601/99; 601/102; 601/115; 601/116; 601/117; 601/118; 601/119; 601/120; 601/121; 601/122; 601/123; 601/124; 601/125; 601/126; 601/127

(58) Field of Classification Search ......... 604/290–293; 601/19, 20, 27, 28, 52, 63, 94, 99, 102, 115–127
See application file for complete search history.

(56) References Cited

U.S. PATENT DOCUMENTS 5,411,470 A * 5/1995 Liptak et al. ................ 601/118

FOREIGN PATENT DOCUMENTS

CN    93222773.2    5/1994
CN    93245731.2    9/1994

* cited by examiner

*Primary Examiner*—Tatyana Zalukaeva
*Assistant Examiner*—Ilya Y Treyger
(74) *Attorney, Agent, or Firm*—Rabin & Berdo, P.C.

(57) ABSTRACT

The hot medicinal compress apparatus is a therapeutic and hearth care medical device which has heating, medicament and rolling functions. It includes a heater (2) and a cartridge (3) carrying a medicinal compress layer. The heater (2) includes a heating element and a heat conducting tube (4) in which the heating element is mounted and at both ends of which a front round step member (10) and a rear round step member (10') having a through hole are respectively arranged; at another end of the front round step member (10), a washer and a demountable baffle ring (18) are provided and fixed by a screw nut (12), while at another end of the rear round step member (10'), a handle (1) is arranged, in which a through hole is provided and on which a control switch is mounted. The cartridge (3) is comprised of a metal tube (17) and a medicinal compress layer which is wrapped around the metal tube (17).

17 Claims, 4 Drawing Sheets

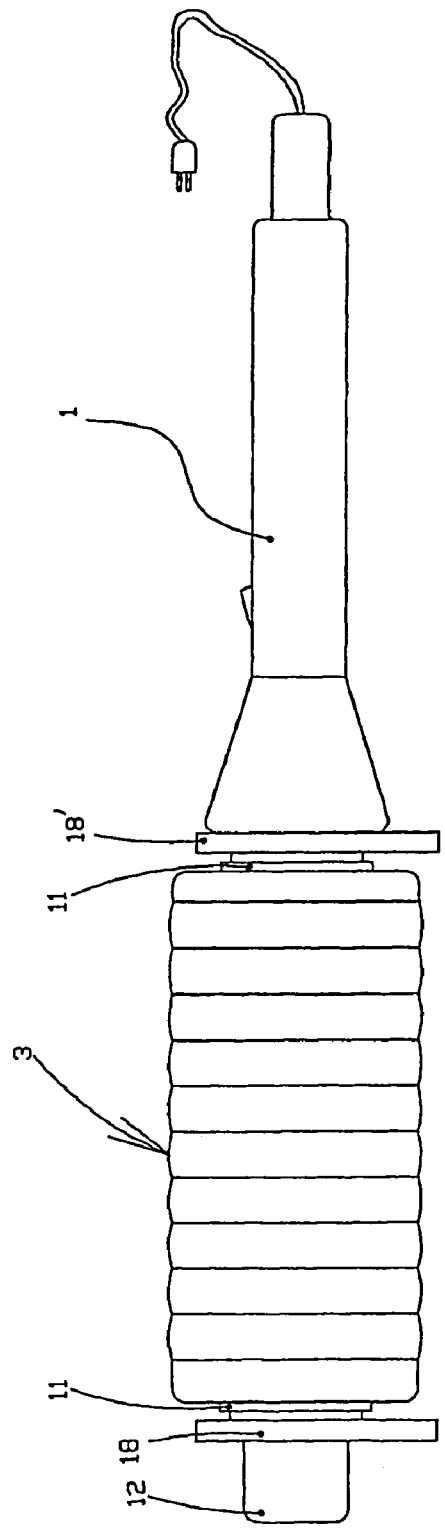
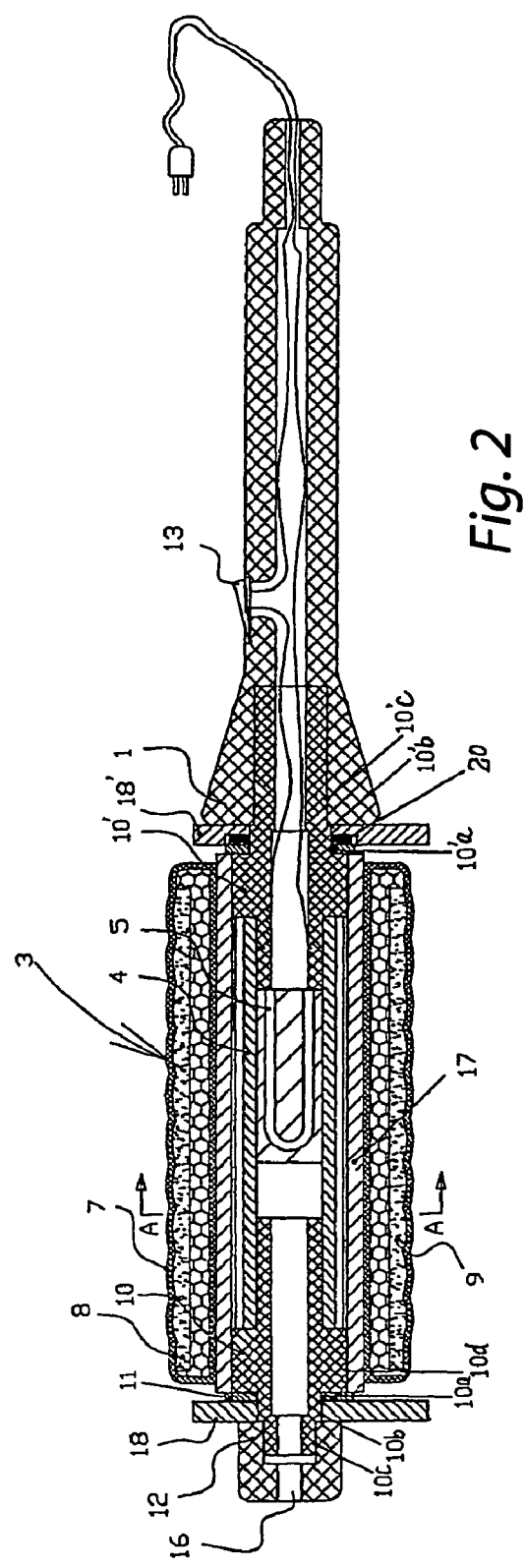
Fig. 1
Fig. 2

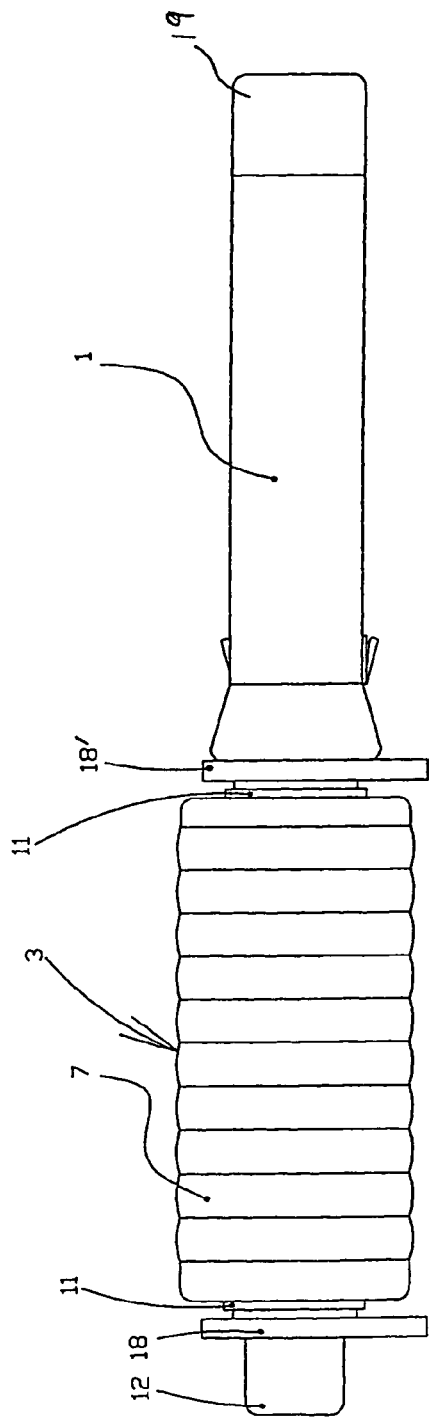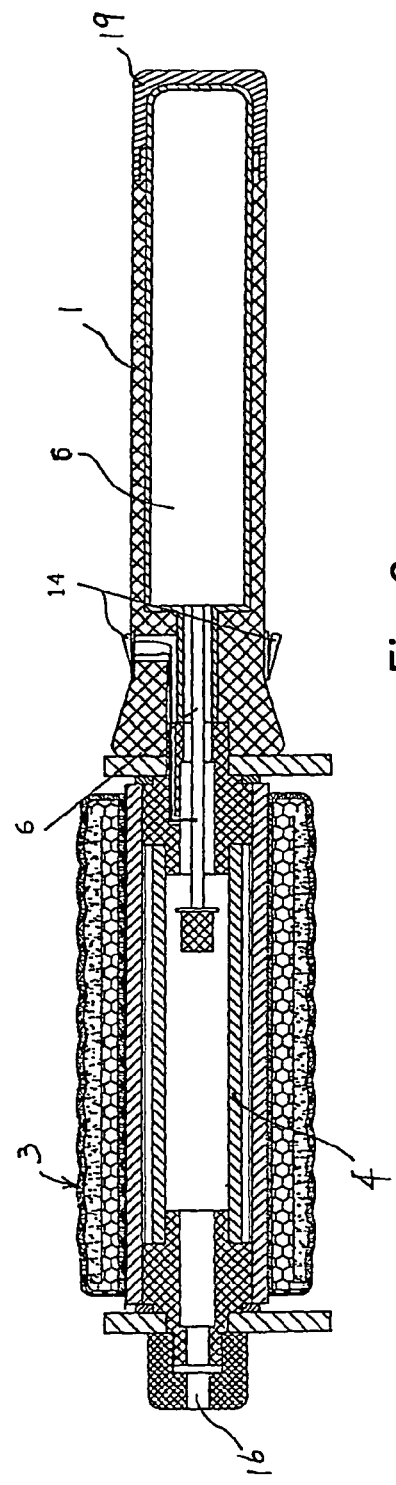

HOT MEDICAL COMPRESS APPARATUS

TECHNICAL FIELD

The invention relates to a hot medicinal compress apparatus, particularly to a hot medicinal compress apparatus comprising a heater and a cartridge, which has heating, medicament and rolling functions. It belongs to medical treatment and health care products.

BACKGROUND OF THE INVENTION

The invention is manufactured based on the principle of "Hot Medicinal Compress Therapy" in the traditional Chinese medicine science. The Hot Medicinal Compress Therapy is one of the external therapeutic methods in the Chinese clinical practice, described in a book entitled "Externally Applying Chinese Herbal Medicine for Health Preserving". This therapy features the "hot compress". That is to say, it helps hair pores of skin sweat gland with the heat applied to open such that the medicine may be percutaneously absorbed through the hair pores in a short time, leading to removal of obstruction in collaterals, improvement on the function of organs, alleviation of cold and coagulation, promotion of blood circulation, relief from pains and elimination of swelling, thus attaining the purpose of prevention and treatment of diseases.

A Chinese patent No. 93222773.2 has disclosed a massage pain releasing device which is a tray-shaped rolling body freely plugged onto a shaft rod, and has a bearing arranged between the shaft rod and the inner hole of the rolling body. The outward projection portion of the shaft rod has a length same as the bearing. Further, a medicated towel is arranged between the rolling body and pain sites of a human body. The medicated towel is made of a material such as cotton or fabric, which is soaked with Chinese herbals having the performances of activating blood circulation and easing pains and which is used after a series of operations such as treatment, drying, steaming. When the shaft rod is pushed by two hands in a translational motion manner, the rolling body will be rolled forward or backward and compress the pain sites or related sites to thereby allow the herbals on the medicated towel to percutaneously penetrate into the pain sites. By means of the combination of the rolling and the penetration of the herbals, removal of obstruction in collaterals, stimulation of blood circulation, ease of pains can be achieved. However, its disadvantages includes:

(1) lack of an automatic heating device, which results in interruption of its rolling operation in order that the medicated towel must be heated separately ever and again and the heated medicated towel must be replaced, thus producing an unfavorable effect on therapeutic or curative effectiveness;

(2) requirement for manual operation with both hands, which is inconvenient to separate the rolling body from the medicated towel during the therapeutic rolling;

(3) rapid loss of heat energy of the medicated towel when the medicated towel is applied on the human body, and bringing about cold if it is not changed timely;

(4) varying the size of medicated towel depending on the affected area of the human body, thus being a need for increasing in consumption of the liquid herbals if the affected area is becoming bigger; and (5) limited application as the device is designed to be used in physical therapy for stimulating circulation of blood and for alleviating pains.

Chinese Patent No. 9324573-1.2 has disclosed a changeable energy-storage medicinal hot-compress implement, including an external housing, a hot compress device and a medicine bag wherein the hot compress device is secured on the external housing; the medicine bag is attached on the hot compress device and is demountably clamped by the external housing. The external housing is made of soft cloth such as cotton cloth, the hot compress device may be an electrocthermal energy storage type hot compress device constructed by a sealed case containing PTC heat sensitive ceramic heating element and thermal insulation material therein, or an external heating energy storage type hot compress device constructed by a sealed case containing energy storage liquids. But such a implement has the following shortcomings including that: (1) it can not be rolled or compressed and can function merely as heat applying, though it has an automatic heating function, consequentially obtaining a weaker effect when compared with that achieved by rolling liquid medicine as well as failing to accomplish comprehensive therapies; (2) its applications are limited by its structure because the medicine bag is relatively small in the heat application area, thus being difficult in treatment of patients having larger affected sites; (3) there is a high requirement for the sealing performance of the housing of the device, because the housing uses liquids as a heat conducting medium, this would increase the manufacturing costs; (4) there is a risk of leakage of liquid medicine, which has unfavourable influence on the heat conduction and also pollutes the patients and the environments.

SUMMARY OF THE INVENTION

It is an object of the invention to provide a hot medicinal compress apparatus having a function of automatic heating and serving as the cartridge of a rolling body which is easy and convenient to plug on, dismount, operate with one hand and which can apply the medicine on the affected sites by rolling. The apparatus can help the sweat gland, blood vessels, hair pores to expand under a combined effect of "heat energy, medicament, and rolling", in such a manner that the medicine may be rapidly percutaneously absorbed and reach the affected sites, leading to removal of obstruction in collaterals, improvement on the function of organs, alleviation of cold and coagulation, promotion of blood circulation, relief from pains and elimination of swelling and inflammation, diminishing of muscle fatigue, thus attaining treatment of diseases and health preservation.

To attain this, the apparatus comprises a heater and a cartridge carrying a medicinal compress layer, characterized in that the heater includes a heating element and a heat conducting tube in which the heating element is mounted and at both ends of which a front round step member and a rear round step member having a through hole are respectively arranged; at another end of the front round step member, a washer and a demountable baffle ring are provided and fixed by a screw nut, while at another end of the rear round step member, a handle is arranged, in which a through hole is provided and on which a control switch is mounted; the heating element is connected with the control switch via the through holes of the rear round step member and the handle; and that the cartridge is comprised of a metal tube, two ends of which is plugged respectively on the front round step member and the rear round step member; and a medicinal compress layer which is formed by medicine powder wrapped in a liquid absorption soft material/cotton cloth and which is wrapped around the metal tube.

Preferably, a layer of strong water absorption material/cotton is arranged between the metal tube and the medicinal compress layer.

The invention may be further improved in a way as follows:

The underside of the front end of the handle is provided with a flat end foot rest which is made integrally with the baffle ring and which is connected with the rear round step member through the baffle ring. A washer with a through hole is arranged between the baffle ring and the cartridge and mounted on a step of the rear round step member which is one step smaller than the maximum step for mounting the cartridge. At another end of said step member, there is also a cylindrical step which is one step smaller than the maximum step and which is secured to the inner hole of one end of the heat conducting tube.

Similar to the rear round step member, the front round step member has a cylindrical step which is one step smaller than the maximum step and is secured to the inner hole of another end of the heat conducting tube. A section of square shaped steps, which are smaller than the diameter of the maximum round step for mounting the cartridge, is extended from another end of the front round step member. A section of screw threads are further extended from the front end of the square shaped steps, equipped with a baffle ring which has a foot rest and is adapted for the square shaped steps and with a screw nut mating with the screw threads. There is a washer with a square hole arranged between the baffle ring and the cartridge and it is also plugged onto the square shaped steps of the front round step member on which the baffle ring is mounted. At the axis of the front round step member and the screw nut fittings, there is a ventilation hole for solving the problem of expanding with heat and contracting with cold in the heat conducting tube when heat is generated from a electrothermal type heater, and for supplementing with air when a combustion gas type heater burns. The washers mounted on the front and rear round step members act as a position limiter for the cartridge to leave a room between the baffle rings and the cartridge. For the cartridge, the cavity of the metal tube has a diameter spatially matched with the diameters of the front and rear round step members, so that the cartridge can rotate freely when it is plugged on the heater.

The heat conducting tube is provided with a plurality of long axial grooves along its outer wall, which, on one hand, can increase the heat-conducting efficiency, and on the other hand, allow the uniform distribution of the heat energy of the cartridge.

Electrothermal tubes or PTC ceramic heaters or the like may be employed as the heating element. In these cases, the heating element is arranged in the heat conducting tube, the power supply wire of which passes through the through hole of the rear round step member and the through hole of the handle to be connected with the power supply switch on the exterior of the handle, and then extended from the tail portion of the handle to be connected with the power supply.

For a combustion gas heater, the handle is provided with a through hole therein and in the through hole a combustion gas storage container is arranged. The handle of the combustion gas heater has a rear cover in its tail portion and a combustion gas switch and electronic igniter on its exterior. A combustion device is mounted in the heat conducting tube, and its fittings are connected with the gas storage container of the handle as well as the combustion gas switch and electronic igniter via the through hole of the rear round step member.

According to the invention, the liquid absorption soft material may be cloth or a soft material having fine and dense meshes, facilitating the wrapping-up of the medicine powder or medicated cloth soaked with medicinal liquids. The strong water absorption material may be selected from cotton, sponge or a material such as cloth having strong water absorption ability, and is placed between the metal tube and the medicine powder in order to prevent the medicine power from being burnt caused by exposure of the medicine power to the heat source for long time, thereby reducing the potent of the medicine.

In use, the cartridge is plugged onto the front and rear round step members respectively connected with two ends of the heat conducting tube of the heater, followed by installation of the front baffle ring and screwing-on of the screw nut. The medicinal liquid is injected into the cotton cloth, the medicine powder and the cotton layers of the cartridge to allow the cartridge to absorb adequately the medicinal liquid. Switch on the power supply control switch of the electrothermal heater or the combustion gas control switch and electronic igniter of the combustion gas heater, such that the heat energy generated by the heating element is transmitted to the heat conducting tube which in turn radiates the heat energy to the cartridge. When the temperature of the cartridge reaches 50~60° C., the handle of the apparatus according to the invention is held by hand to apply the cartridge on the affected sites and the relevant acupoints of a patient. Subsequently, push the handle with an appropriate force to allow the rotation of the cartridge about the front and rear round step members connected with the two ends of the heat conducting tube as a rotating shaft, in such a rolling way to performing treatment of diseases.

The invention produces beneficial effects. For examples, (1) it facilitates the expansion of the sweat gland, hair pores and blood vessels to allow the medicine to be absorbed rapidly at the affected sites with an increased therapeutic efficiency, because the apparatus of the invention has the function of automatic heating and is also provided with the handle and the cartridge, making its rolling operation easy and convenient and thus achieving a combination of "heat energy, medicament, and rolling"; (2) it allows the application of the "Hot Medicinal Compress Therapy" in the traditional Chinese medical practice to become more simple and convenient by use of a selected cartridge directed against the conditions or symptoms to perform the hot medicinal compress therapy on the human body, this can not only lead to removal of obstruction in collaterals, relief from pains and elimination of inflammation and swelling, diminishing of muscle fatigue, but also to improvement on the function of organs, alleviation of cold and coagulation, promotion of blood circulation, thus attaining treatment of diseases and health preservation; (3) there is no need for considering the specifications and sizes of the cartridges in the manufacturing progress, because the size of the cartridge would not vary with the affected area of a patient when performing the "Hot Medicinal Compress Therapy"; (4) it is easy and convenient to operate, particularly with one hand, there is no difficulty in plugging on and removing the cartridge from the heater whenever necessary, and its replacement is also simple and rapid.

To have a better understanding of the invention reference is made to the following detailed description of the invention and embodiments thereof in conjunction with the accompanying drawings.

BRIEF DESCRIPTION OF THE DRAWINGS

FIG. 1 is a schematic view of the outer appearance structure of a first embodiment of the invention which using electric power as a heat source.

FIG. 2 is a schematic main sectional view of the first embodiment.

FIG. 8 is a schematic view of the outer appearance structure of a second embodiment of the invention which using combustion gas energy as a heat source.

FIG. 9 is a schematic main sectional view of the second embodiment.

Figure 3:
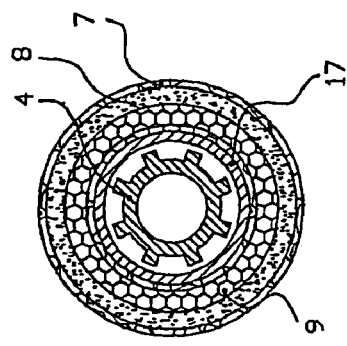
FIG. 3 is schematic sectional view along A-A line of FIG. 2.

In the above accompanying drawings, the reference numbers for the various members and/or devices are set out as follows:

plastic handle 1; heater 2; cartridge 3; heat conducting tube 4; electrothermal type heating element 5; combustion gas heat type heating element 6; soft and tenacious liquid absorption material/cotton cloth 7; medicine powder 8; strong water absorption material/cotton 9; front round step member 10 having steps 10$a$, 10$b$, 10$c$; diameter portion 10$d$ of the front round step member for supporting the cartridge; rear round step member 10' having steps 10'$a$, 10'$b$, 10'$c$; diameter portion 10'$d$ of the rear round step member for supporting the cartridge; stainless steel washer 11; screw nut 12; power supply switch 13; combustion gas switch and electronic igniter 14; combustion gas storage container 15; ventilation hole 16; metal tube 17; front baffle ring 18; rear baffle ring 18'; rear cover 19; sealing ring 20.

DETAILED DESCRIPTION OF THE PREFERRED EMBODIMENTS

Figure 4:
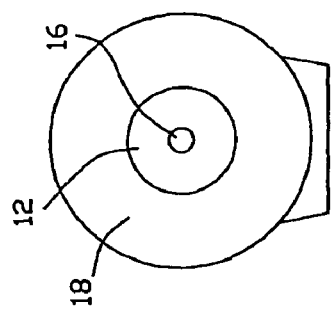
FIG. 4 is a schematic left view of FIG. 2.
Figure 5:
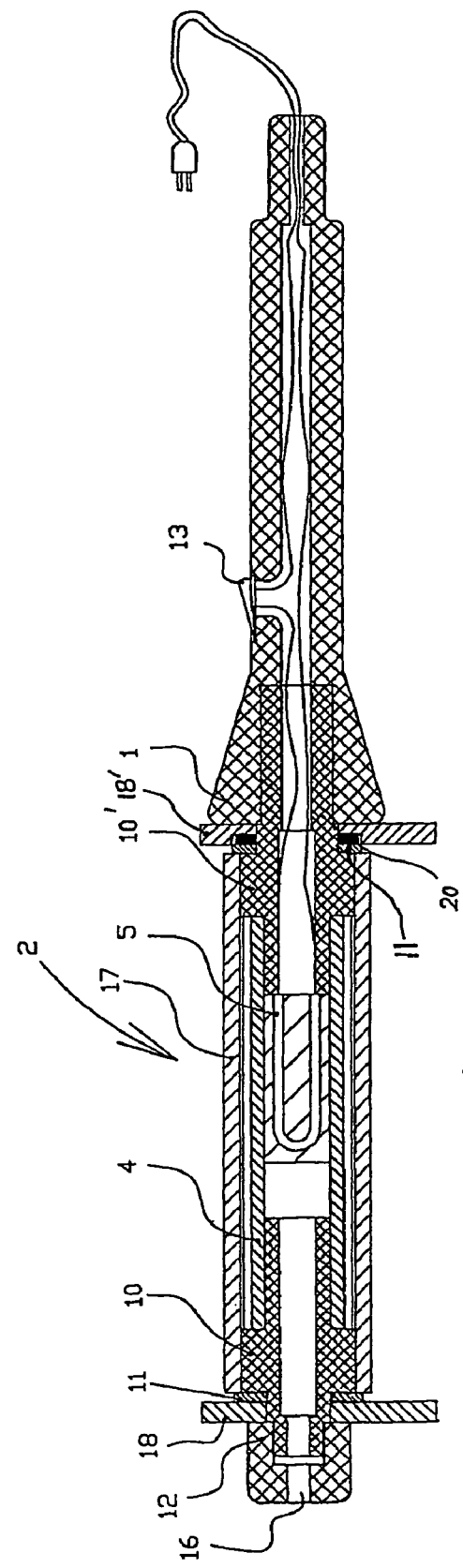
FIG. 5 is a schematic sectional view of the heater consistent with the first embodiment.
Figure 6:
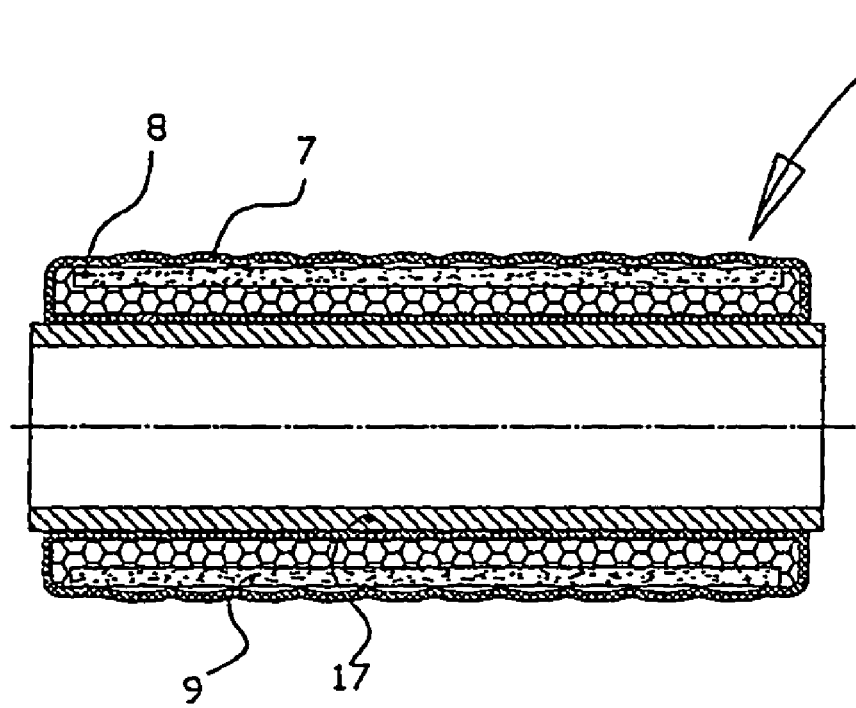
FIG. 6 is a schematic sectional view of the cartridge.
Figure 7:
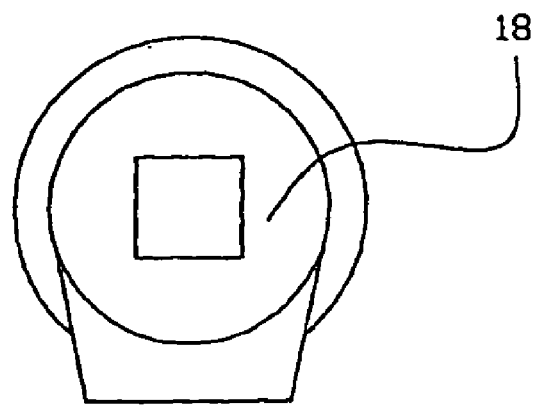
FIG. 7 is a schematic main view of the baffle ring having a foot rest and a stainless steel washer arranged therein.

Referring now to FIGS. 1 to 7, a hot medicinal compress apparatus which using electric power as a heat source is provided consistent with a first embodiment of the present invention. In this embodiment, the apparatus comprises a heater 2 and a medicine bag 3, wherein the medicine bag 3 is constructed by a soft and tenacious liquid absorption material 7 which wraps up medicine powder 9 or a medicated cloth, in combination with a strong water absorption material 8. The liquid absorption soft material 7 may be selected from cloth materials, the water absorption material 8 may be selected from cotton or cotton yarn; and the medicine powder is putted over the cotton or cotton yarn, or as an alternative, a medicated cloth soaked with a medicinal liquid is putted over the cotton or cotton yarn, followed by wrapping them up in the liquid absorption material 7 (e.g. cotton cloth), with the cotton or cotton yarn as the lower face of the medicine bag. When wrapping the metal tube 17 with the medicine bag 3, the metal tube is arranged to come contact with the lower face of the medicine bag in order to prevent the medicine power from being burnt caused by exposure of the medicine power to the heat source for long time, thereby reducing the potent of the medicine.

In a more specific scheme, the cartridge comprises: the metal tube 17; a first layer of the liquid absorption soft material/cotton cloth 7 which wrapping up the strong water absorption material/cotton 9, said first layer being wrapped around the outer wall surface of the metal tube 17; and a second layer of the liquid absorption soft material/cotton cloth 7 which wrapping up the medicine powder 8 in a manner that the medicine power leak would not take place, said second layer being wrapped around the outer surface of the first layer so that the strong water absorption material/cotton 9 is arranged between the medicine powder 8 and the metal tube 17. An example of such a cartridge is made by a process comprising the steps of: putting the strong water absorption material/the cotton over the middle area of the front half section of a square cotton cloth and putting the medicine powder over the middle area of the rear half section of the cotton cloth; folding up the left and right sides of the cotton cloth in light of the length of the metal tube so as to form a cloth strip in which the cotton and the medicine powder are wrapped, the width of said cloth strip being preferably equal to the length of the metal tube; and wrapping the surface of the metal tube with the cloth strip from its front section to its rear section. The cotton layer is arranged between the medicine powder and the metal tube with the purpose of preventing the medicine power from being burnt caused by direct contact of the medicine power with the metal tube for long time, thereby reducing the potent of the medicine.

The heater 2 comprises a handle 1, a heating element 5, a metal tube 17, a heat conducting tube 4 having a plurality of axial protrusion ribs on the tube wall thereof, front and rear round step members 10 and 10', a screw nut 12, a stainless steel washer 11, front and rear baffle rings 18 and 18'. The heating element 5 is an electrothermal tube and is mounted in the heat conducting tube 4. The plurality of protrusion ribs are provided and evenly spaced along the circumference on the outer wall of the heat conducting tube 4 and the heat conducting tube is connected with the handle 1 via the rear round step member 10' having a through hole along the central axis. The rear round step member 10' is a cylindrical body having at least one round step at each of its two ends, one end of which has three steps 10'$a$, 10'$b$, 10'$c$, and the outer most end is the round step 10'$c$ which has the minimum profile and is fixed in the mounting hole at the front end of the handle 1. The step 10'$b$ adjacent to the step 10'$c$ is a square step on which a rear baffle ring 18' having a foot rest is mounted (see FIG. 7). The rear baffle ring 18' is an integrated body formed by a circular ring portion and a trapezoid portion wherein the trapezoid portion is the foot rest having a flat end 18'$a$ at its lower end, by which the foot rest can be placed firmly on the platform to support the heater. The step 10'$a$ has the same size and shape as the step 10'$b$, on which a stainless steel washer 11 is mounted. The washer 11 has an outer diameter slightly larger than the maximum diameter portion 10'$d$ of the rear round step member 10', serving as a position limiter to the metal tube 17 which is plugged on the maximum diameter portion of the step member to allow to leave a room between the metal tube 17 and the rear baffle ring 18' in order to avoid generation of the friction when the metal tube 17 rotates. Another end of the rear round step member (i.e. the internal end) has only one round step which is connected fixedly with the heat conducting tube 4. The rear round step member 10' has a through hole in communication with the through hole of the handle and with the inner cavity of the heat conducting tube 4, in such a manner that the connection wire of the heating element 5 can pass through the central through holes in communication with each other.

Likewise, another end of the heat conducting tube (i.e. the external end) is also fixedly connected to the internal end step of the front round step member 10 which is symmetrically shaped with the rear step member 10'. The metal tube 17 has a length adapted for the distance between the two ends of the heat conducting tube 4 plus the combined length of the maximum diameter portions of the front and rear round step members, and it is respectfully plugged on the maximum diameter portions 10$d$, 10'$d$ of the front and rear round step members. Their dimensions are devised to be spatially matched with each other to allow the rotation of the metal tube. The front round step member 10 acts also as a stopper for the external end (cover) of the metal tube. Similar to the rear round step member 10', another end of the front round step member 10 (i.e. the external end) has three steps 10$a$, 10$b$, 10$c$ from in to out, these steps 10*a*, 10*b*, 10*c* is respectively provided with the stainless steel washer 11, the front baffle ring 18 having a foot rest and a screw thread connection (i.e. the screw nut 12) which is used for fastening the baffle ring by connection with the screws of the smallest step. In this way, the front baffle ring 18, the neighboring stainless steel washer 11 and the metal tube 17 may be easily removed. The front and rear baffle rings, each of which has a foot rest, allow the hot medicinal compress apparatus of the invention to be placed on a table. The screw nut has an air ventilation hole 16 in communication with the through hole of the front round step member for solving the problem of expanding with heat and contracting with cold in the heat conducting tube. The cartridge is made by wrapping the outer surface of the metal tube 17 of the heater with the medicine bag.

The invention is preferably used in combination with a bottled medicine liquid which is a effective cure for the conditions or symptoms, in order to promote the potent of the medicine powder.

Preferably, the handle 1 is made of plastic material, on which there is a power supply switch 13. The electric wire of the heating element 5 is connected with the switch 13 via the through holes of the rear round step member 10' and the handle 1.

Preferably, the front and rear step members 10, 10' are made of plastic materials with resistance to high temperature, for the purpose of enhancing electricity insulation and heat insulation as well as supporting the cartridge to allow the free rotation of the cartridge on the heat conducting tube. The demountable washer, baffle ring and screw nut are provided to allow the cartridge to rotate on the support of the round step members so as not to come out.

Due to the rolling of the medicinal liquid during the operation, there is a possibility that the medicinal liquid may overflow and permeates into the heater thereby to form a short circuit. In order to avoid this, the sealing ring 20 is arranged between the baffle ring and the stainless steel washer to prevent the medicinal liquid from permeating into the handle though the gaping.

The present invention is advantageously used in combination with a bottled medicine liquid to facilitate the potent of the medicine.

In FIG. 8-9, a hot medicinal compress apparatus is provided consistent with a second embodiment of the present invention. This embodiment provides the apparatus significantly differing in that combustion gas energy is used as a heat source. In this embodiment, the heating element is a combustion gas type heating element 6; a combustion gas storage container is arranged in the through hole of the handle, and a rear cover 19 is also provided on the handle; the combustion gas heating element 6 is mounted in the heat conducting tube 4, the fittings of the heating element 6 are connected with the gas storage container of the handle and the combustion gas switch and electronic igniter by passing through the though hole of the rear round step member. After the combustion gas switch and electronic igniter 14 is switched on, the combustion gas burns the heat conducting tube to heat the cartridge 3. The air ventilation hole 16 in the center of the screw nut is provided to keep communication with the through hole of the front round step member for supplementing with air the heating element in the heat conducting tube 4 during the combustion.

It is understood that many other embodiments of the present invention are also possible, and many corresponding modifications as well as variations can be made by those skills in the art as according to the disclosure of the present invention and without departing from the spirits and essentials thereof, while such modifications and variations fall into the scope of the claims of the present invention.

What is claimed is:

1. A hot medicinal compress apparatus comprising a heater (2) and a cartridge (3) carrying a medicinal compress layer, characterized in that:

the heater (2) includes a heating element and a heat conducting tube (4) in which the heating element is mounted and at both ends of which a front round step member (10) and a rear round step member (10') having a through hole are respectively arranged; at another end of the front round step member (10), a washer and a demountable baffle ring (18) are provided and fixed by a screw nut (12), while at another end of the rear round step member (10'), a handle (1) is arranged in which a through hole is provided and on which a control switch is mounted; the heating element is connected with the control switch via the through holes of the rear round step member (10') and the handle (1); and the cartridge (3) is comprised of:

a metal tube (17), two ends of which is plugged respectively on the front round step member (10) and the rear round step member (10'), and a medicinal compress layer which is formed by medicine powder (8) wrapped in a liquid absorption soft material/cotton cloth (7) and which is wrapped around the metal tube (17).

2. The apparatus as claimed in claim 1, characterized in that the heat conducting tube (4) has a plurality of axial grooves on the outer wall thereof; the rear round step member (10') is a cylindrical body having at least one round step at each of its two ends, one end of which has two or more steps, the step with minimum profile Lies on the most outer thereof and is fixed in the mounting hole at the front end of the handle (1); the step adjacent to the step 10'*c* is a square step, on which a rear baffle ring (18') having a foot rest is provided, and the rear baffle ring (18') is an integrated body formed by a circular ring portion and a trapezoid portion wherein the trapezoid portion is the foot rest having a flat end at its lower end; another end of the rear round step member (10') has only one step which is connected and tightly fastened in the inner hole of one end of the heat conducting tube (4); the maximum diameter portion (10'*d*) of the rear round step member serves for supporting the cartridge (3); and the through hole of the rear round step member (10') is in communication with the through hole of the handle (1).

3. The apparatus as claimed in claim 2, characterized in that the front round step member (10) has the same structure as the rear round step member (10') and is symmetrically mounted on the heat conducting tube; two or more steps are provided at the external end portion of the metal tube wherein the baffle ring (18) is arranged on the larger square step (10*b*), and screw threads are provided on the smaller round step (10*c*) for connection with the screw nut (12) so as to fasten the baffle ring; and the maximum diameter portion (10'*d*) of the front round step member serves for supporting the cartridge (3); another end of the front round step member (10) has only one step which is connected and fastened to the inner hole of another end of the heat conducting tube (4).

4. The apparatus as claimed in claim 3, characterized in that the front and rear round steps further have respective steps (10*a*, 10'*a*) larger than the square steps, for mounting a washer (11), the outer diameter of which is slightly larger than the maximum diameter portion of the rear round step member (10') and which serves as a position limiter to the metal tube (17) plugged on the maximum diameter portion of the step member to allow to leave a room between the metal tube (17)

and the rear baffle ring (18'); the cartridge (3) has a length consistent with the distance between the two ends of the heat conducting tube (4) plus the combined length of the maximum diameter portions of the front and rear round step members, i.e. the distance between the two washers, the cavity diameter of the metal tube (17) and the diameter portions (10*d*, 10'*d*) of the front and rear round step members are devised to be spatially matched with each other to allow the flexible rotation of the cartridge (3) plugged on the front and rear round steps at the two ends of the heat conducting tube; and a sealing ring (20) is arranged between the baffle ring (18') and the washer.

5. The apparatus as claimed in claim 4, characterized in that the steps (10 *a*, 10'*a*) and the steps (10*b*, 10'*b*) of the front and rear round step members have the same size and profile and they are manufactured integrally.

6. The apparatus as claimed in claim 1, characterized in that the heating element is an electrothermal type heating element (5) which is mounted in the heat conducting tube (4), the electric wire passes through the though holes of the rear round step member (10') and the handle (1) to be connected with the power supply control switch (13).

7. The apparatus as claimed in claim 1, characterized in that the heating element is a combustion gas type heating element (6) which is mounted in heat conducting tube (4), and its fittings pass through the though holes of the rear round step member (10') and the handle (1) to be connected with a combustion gas switch and electronic igniter (14).

8. The apparatus as claimed in claim 1, characterized in that a layer of strong water absorption material/cotton (9) is arranged between the metal tube (17) and the medicinal compress layer.

9. The apparatus as claimed in claim 2, characterized in that the heating element is an electrothermal type heating element (5) which is mounted in the heat conducting tube (4), the electric wire passes through the though holes of the rear round step member (10') and the handle (1) to be connected with the power supply control switch (13).

10. The apparatus as claimed in claim 3, characterized in that the heating element is an electrothermal type heating element (5) which is mounted in the heat conducting tube (4), the electric wire passes through the though holes of the rear round step member (10') and the handle (1) to be connected with the power supply control switch (13).

11. The apparatus as claimed in claim 4, characterized in that the heating element is an electrothermal type heating element (5) which is mounted in the heat conducting tube (4), the electric wire passes through the though holes of the rear round step member (10') and the handle (1) to be connected with the power supply control switch (13).

12. The apparatus as claimed in claim 2, characterized in that the heating element is a combustion gas type heating element (6) which is mounted in heat conducting tube (4), and its fittings pass through the though holes of the rear round step member (10') and the handle (1) to be connected with a combustion gas switch and electronic igniter (14).

13. The apparatus as claimed in claim 3, characterized in that the heating element is a combustion gas type heating element (6) which is mounted in heat conducting tube (4), and its fittings pass through the though holes of the rear round step member (10') and the handle (1) to be connected with a combustion gas switch and electronic igniter (14).

14. The apparatus as claimed in claim 4, characterized in that the heating element is a combustion gas type heating element (6) which is mounted in heat conducting tube (4), and its fittings pass through the though holes of the rear round step member (10') and the handle (1) to be connected with a combustion gas switch and electronic igniter (14).

15. The apparatus as claimed in claim 2, characterized in that a layer of strong water absorption material/cotton (9) is arranged between the metal tube (17) and the medicinal compress layer.

16. The apparatus as claimed in claim 3, characterized in that a layer of strong water absorption material/cotton (9) is arranged between the metal tube (17) and the medicinal compress layer.

17. The apparatus as claimed in claim 4, characterized in that a layer of strong water absorption material/cotton (9) is arranged between the metal tube (171) and the medicinal compress layer.

* * * * *